United States Patent [19]

Saltzman

[11] 3,957,983

[45] May 18, 1976

[54] PREVENTION OF TOXICITY ACCOMPANYING ADMINISTRATION OF 3,7-DISUBSTITUTED BILE ACIDS

[75] Inventor: William H. Saltzman, New Rochelle, N.Y.

[73] Assignee: Intellectual Property Development Corporation, New Rochelle, N.Y.

[22] Filed: Mar. 12, 1975

[21] Appl. No.: 557,685

[52] U.S. Cl. ............................................. 424/240
[51] Int. Cl.$^2$ ................ A61K 31/56; A61K 31/575
[58] Field of Search ............................. 424/240, 181

[56] References Cited
OTHER PUBLICATIONS

Hofmann et al. – Chem. Abst. Vol. 68 (1968) p. 76820S.

*Primary Examiner*—Sam Rosen

[57] ABSTRACT

A method for reducing or preventing toxicity in mammals which comprises administering to said mammal a small but effective amount of an antibiotic either prior to or concurrently with the administration to said mammal of a compound of the formula

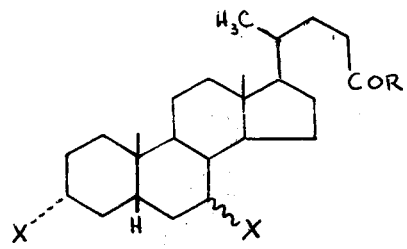

wherein each X is selected from the group consisting of hydroxy, acyloxy, alkoxy or oxo (O=); and R is selected from the group consisting of hydroxy, acyloxy, alkoxy or an amino acid conjugate, such as glycine or taurine.

8 Claims, No Drawings

PREVENTION OF TOXICITY ACCOMPANYING ADMINISTRATION OF 3,7-DISUBSTITUTED BILE ACIDS

Recently, it has been discovered that compounds of the formula (I)

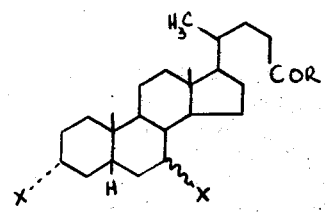

wherein each X may be hydroxy, acyloxy, alkoxy or oxo (O=); and R is hydroxy, acyloxy, alkoxy or an amino acid conjugate such as taurine or glycine; are therapeutically useful in the treatment of various diseases. In U.S. Pat. No. 3,859,437, it is disclosed that such compounds have been found useful to lower cholesterol levels of patients, including the ability to dissolve cholesterol gallstones while at the same time preventing or avoiding a concomitant elevation of cholesterol levels. However, in the course of various investigations with the compounds of this invention, related to their therapeutic utility, a number of investigators have discovered that there is an incidence of hepatotoxicity which may be attendant to the administration of the compounds to the animal being tested. For example, it has been reported that upon administration to certain primates, of chenodeoxycholic acid (3α, 7α-dihydroxy-5β-cholanic acid) there is a significant incidence of hepatotoxicity in the animals tested therewith, especially in those cases where higher dosage levels are employed, for example, in excess of 10 mg per kilo of body weight of the animal being tested. The reason for the toxicity has until now not been fully understood, nor has any cure or prophylactic treatment therefor been available.

I have now discovered a method for substantially reducing and in many cases totally preventing the hepatotoxicity in mammals to whom therapeutic amounts of compounds of the formula (I)

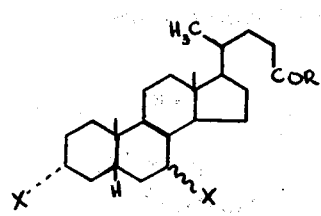

wherein X and R are as defined above, have been administered over an extended period of time.

More particularly, I have discovered that the attendant toxicity which arises upon the administration of the compounds of formula I to mammals, can be substantially reduced or prevented by the prior or concurrent administration of a small but effective amount of a suitable antibiotic to the mammal being treated. On the basis of this finding, it is suggested that the cause of the hepatotoxicity experienced upon the administration of the compounds of formula I, is not caused directly by the compound itself, but rather by some microorganism endogenous to the mammal being treated, which metabolizes or otherwise converts the compound of formula I into a substance which causes toxicity. This invention resides in the finding that the administration of a small but effective amount of an appropriate antimicrobial material, an antibiotic, either prior to or concurrently with the compounds of formula I, sufficiently controls or totally eliminates the microorganisms which are directly related to the causation of toxicity and thus substantially reduces or eliminates such toxicity, thus enhancing the therapeutic properties of the compounds of formula I.

(It should be noted that in this Specification and in the Claims appended thereto, whenever a curved line ($\xi$) is employed in the linkage of atoms in the structural formulae set forth therein, it is meant to denote that the attached moiety may be in either the α or β-position as the case may be.)

When employed in this Specification and the Claims appended hereto, the term acyl is meant to denote an acyl group derived from a hydrocarbon carboxylic acid of less than 12 carbon atoms and includes such hydrocarbon carboxylic acids as the alkanoic, alkenoic, monocyclic cycloakane, the monocyclic acyl and monocyclic cycloalkene carboxylic acids, for example, propionic or butenoic acids, cyclohexanoic or cyclohexenoic acids, or phenylacetic or benzoic acids.

The term alkyl as employed herein is meant to denote and include alkyl groups of less than 7 carbon atoms and includes such alkyl groups as methyl, ethyl and butyl.

Among the compounds of formula I which have been found to be involved in the satisfactory practice of this invention may be specifically included such compounds as, 3α, 7α-dihydroxy -5β-cholanic acid; 3α, 7β-dihydroxy -5β-cholanic acid; 3α, 7α-diacyloxy -5β-cholanic acid; 3, 7-dioxo-5β-cholanic acid; the taurine or glycine conjugates of these compounds, and the non-toxic pharmaceutically acceptable salts thereof. Most specifically, most satisfactory results are obtained in the practice of this invention when the compounds of formula I are 3α, 7α-dihydroxy-5β-cholanic acid; 3α, 7α-dihydroxy -5β-cholanic acid, the glycine or taurine conjugates thereof, or the non-toxic, pharmaceutically acceptable salts thereof although satisfactory results may be obtained with the other compounds also.

Satisfactory results have been obtained in the practice of this invention when a small but effective amounts of the antibiotic of this invention are administered either prior to or concurrently with the compounds of formula I to the mammal being treated. The compounds of formula I are usually administered to the mammal being treated at a daily dosage level equal to form about 5 mg/kilo of body weight over an extended period of time. The antibiotic of this invention may be administered, preferably periodically, at a dosage level sufficient to provide the mammal being treated with from about 0.005 grams to about 3.0 grams per day, depending upon the antibiotic employed and the mammal being treated. More specifically, satisfactory results may be obtained when the antibiotic of this invention is perorally administered to the mammal being treated, either in the form of capsules or liquid solutions or suspensions or elixirs, in an amount sufficient to provide a daily dosage of said antibiotic of from about 0.01 to about 1.5 grams. In addition, the antibiotic may be administered to the mammal being treated, for a period prior to the administration of the compounds of formula I, for a short period concurrently with the administration of the compounds of formula I, or during the course of therapy with the compounds of formula I, all without deviating from the successful practice of the instant invention. In practice however, it has been found most convenient to administer the antibiotic for a short period prior to and a short period after inception of the regimen of administration of the compounds of formula I. However, the most satisfactory mode and time of administration can be chosen by the skilled worker depending upon the active substances to be employed in and the mammal being treated in accordance with the teachings and practice of the instant invention.

The antibiotics which may be employed in the satisfactory practice of the instant invention include those which are active against the gram-positive or gram-variable and preferably anaerobic microorganisms and include such antibiotics as doxycycline, lincomycin, clindamycin, neomycin, tetracyclines and their derivatives, cephalothins, among others. Most satisfactory results have been obtained when lincomycin has been utilized in the practice of this invention, although the others also give satisfactory results.

The invention may be illustrated by the following Example.

EXAMPLE 1

A group of Rhesus Monkeys were separated into 4 separate sub-groups. To each of these sub-groups was administered an amount of $3\alpha$, $7\alpha$-dihydroxy-$5\beta$-cholanic acid, except for one sub-group which was maintained as a control group and to which was administered a placebo. One of the treated sub-groups was treated solely with $3\alpha$, $7\alpha$-dihydroxy-$5\beta$-cholanic acid. To one of the 2 remaining sub-groups was administered 15 mg. per day of lincomycin commencing one month prior to administration of the $3\alpha$, $7\alpha$-dihydroxy-$5\beta$-cholanic acid and concurrent feeding of both materials was continued for a period of 6 months. The the remaining group was administered 15 mg. of lincomycin daily commencing one month prior to the administration of the $3\alpha$, $7\alpha$-dihydroxy-$5\beta$-cholanic acid and feeding thereof was continued for one month after bile acid treatment was begun, and bile acid treatment continued for an additional 5 months. At the end of the 6 month feeding study, the test animals were sacrificed and autopsied and liver toxicity levels were determined. The results obtained are set forth in Table 1 below:

TABLE 1

| Group | Treatment | Dosage[1] | Result |
|---|---|---|---|
| 1 | Control | 0 | No Toxicity |
| 2 | CDCA* | 40–100 mg/kg | Moderate to Severe Hepatotoxicity |
| 3 | L + CDCA** | 40–100 mg/kg | No Toxicity |
| 4 | L*** L + CDCA | 40–100 mg/kg | None to Slight Hepato- |
| | CDCA | | toxicity |

[1]CDCA
*CDCA = $3\alpha$, $7\alpha$-dihydroxy-$5\beta$-cholanic acid
**L + CDCA = Lincomycin plus $3\alpha$, $7\alpha$-dihydroxy-$5\beta$-cholanic acid.
***L
L+CDCA = 1 month lincomycin
CDCA 1 month lincomycin plus $3\alpha$, $7\alpha$-dihydroxy-$5\beta$-cholanic acid 5 months - $3\alpha$, $7\alpha$-dihydroxy-$5\beta$-cholanic acid The foregoing studies demonstrate that the prior and concurrent administration of an antibiotic with $3\alpha$, $7\alpha$-dihydroxy -$5\beta$-cholanic acid substantially reduces or eliminates the toxicity attendant upon the administration of $3\alpha$, $7\alpha$-dihydroxy -$5\beta$-cholanic acid alone.

The invention may be variously otherwise embodied within the scope of the appended claims.

What is claimed is:

1. A method for reducing or preventing toxicity in mammals which comprises administering to said mammal a small but effective amount of an antibiotic effective against gram-positive or gram-variable microorganisms either prior to or concurrently with the administration to said mammal of a compound of the formula:

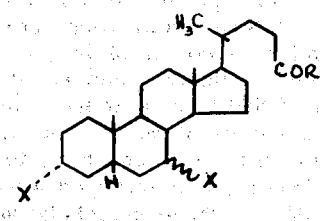

wherein each X is selected from the group consisting of hydroxy, acyloxy, alkoxy or oxo (O=), and R is selected from the group consisting of hydroxy, acyloxy, alkoxy, taurine or glycine, and the non-toxic, pharmaceutically acceptable salts thereof.

2. The method of claim 1, wherein the compound is $3\alpha$, $7\alpha$-dihydroxy-$5\beta$-cholanic acid.

3. The method of claim 1, wherein the antibiotic is lincomycin.

4. A composition useful to prevent toxicity which comprises a combination of an antibiotic effective against gram-positive or gram-variable microorganisms and a compound of the formula

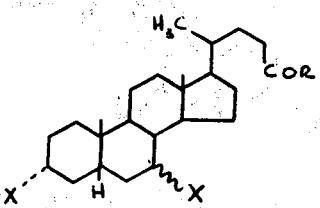

wherein X and R are as defined in claim 1.

5. The composition of claim 4 wherein the compound is $3\alpha$, $7\alpha$-dihydroxy-$5\beta$-cholanic acid.

6. The composition of claim 4, wherein the antibiotic is lincomycin.

7. The method of claim 1, wherein the antibiotic is selected from the group consisting of doxycycline, lincomycin, clindamycin, neomycin, tetracyclines and cephalothins.

8. The composition of claim 4, wherein the antibiotic is selected from the group consisting of doxycycline, lincomycin, clindamycin, neomycin, tetracyclines and cephalothins.

* * * * *